United States Patent [19]
Lacefield et al.

[11] 4,197,313
[45] Apr. 8, 1980

[54] ANTIARRHYTHMIC METHOD

[75] Inventors: William B. Lacefield, Indianapolis; Richard L. Simon, Greenwood, both of Ind.

[73] Assignee: Eli Lilly and Company, Indianapolis, Ind.

[21] Appl. No.: 19,535

[22] Filed: Mar. 12, 1979

[51] Int. Cl.$^2$ .................. A61K 31/275; A61K 31/135
[52] U.S. Cl. ............................... 424/304; 424/248.54; 424/248.55; 424/248.57; 424/267; 424/274; 424/324; 424/329; 424/330
[58] Field of Search ...................... 424/248.54, 248.55, 424/248.57, 262, 274, 304, 329, 330, 324; 260/558 A

[56] References Cited

U.S. PATENT DOCUMENTS

| | | | |
|---|---|---|---|
| 3,476,545 | 11/1969 | Mohr et al. | 71/76 |
| 3,660,485 | 5/1972 | Cusic et al. | 260/558 H |
| 3,843,657 | 10/1974 | Lowrie | 260/268 T |
| 4,001,328 | 1/1977 | Molloy | 260/567.6 M |

FOREIGN PATENT DOCUMENTS 960758  6/1964  United Kingdom .

OTHER PUBLICATIONS

Chemical Abstracts 61: 8267a (1964).
Chemical Abstracts 59: 13906h (1963).
Chemical Abstracts 64: 14199h (1966).
Chemical Abstracts 55: 27340b (1961).
Gautier et al., Bull. Soc. Chim. France, 1965 (II), 3162–3169.

Primary Examiner—Leonard Schenkman
Attorney, Agent, or Firm—Charles W. Ashbrook; Arthur R. Whale

[57] ABSTRACT

Cardiac arrhythmias are treated with 9-aminoalkyl-9-(hydroxy, cyano, or carbamoyl)-fluorenes.

21 Claims, No Drawings

ANTIARRHYTHMIC METHOD

BACKGROUND OF THE INVENTION

This invention concerns a method for treating cardiac arrhythmias utilizing 9, 9-disubstituted fluorenes.

Cardiovascular disorders are the cause of thousands of deaths each year. Cardiac arrhythmias are among such disorders. Arrhythmias are irregular cardiac activity characterized by irregular beating of the heart. Typical arrhythmias include VF or ventricular fibrillation, ventricular tachycardia, auricular flutter and auricular fibrillation.

A number of drugs are known which display varying degrees of antiarrhythmic activity. Quinidine, procainamide, lidocaine and digitalis are perhaps among the most widely used antiarrhythmic agents. Recent research has developed improved antiarrhythmic agents such as aprindine, bretylium and certain diphenylbutanolamines; see U.S. Pat. No. 4,001,328.

Cusic, in U.S. Pat. No. 3,660,485, discloses certain fluorene-9-carboxylic acid hydrazides which allegedly are useful as antiarrhythmic agents. Numerous other fluorenes are known in the art, but none are reported to have antiarrhythmic activity. Stack, for example, discloses several 9-(3-tertiary aminopropyl)-9-hydroxyfluorenes which are intermediates leading to 9-alkylidene fluorenes, which in turn are neuroleptic agents; see British Pat. No. 960,758. Lowrie, in U.S. Pat. No. 3,843,657, discloses 9-dialkylaminoalkylfluorene-9-N-substituted carboxamides which allegedly are anti-bacterial and anti-fungal agents.

An object of this invention is to provide a method for treating cardiac arrhythmia with 9-aminoalkylfluorenes which are 9-hydroxy, 9-cyano, 9-aminocarbonyl or 9-substituted aminocarbonyl compounds.

Summary of the Invention

This invention concerns a method of treatment. The invention provides a method for treating cardiac arrhythmias comprising administering to a subject suffering from an arrhythmia and in need of treatment or to a subject suspected of developing a cardiac arrhythmia an antiarrhythmic amount of an aminoalkylfluorene of the formula

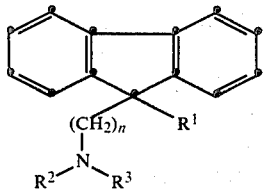

wherein:

$R^1$ is hydroxy, cyano, or $CONR^4R^5$ in which $R^4$ and $R^5$ independently are hydrogen or $C_1$-$C_6$ alkyl; n is 2, 3 or 4;

$R^2$ and $R^3$ independently are hydrogen, $C_1$-$C_6$ alkyl, $CH_2C_2$-$C_5$ alkenyl, phenyl-$C_1$-$C_3$ alkyl, or taken together are $C_4$-$C_5$ alkylene or -$CH_2CH_2OCH_2CH_2$-; and the pharmaceutically acceptable acid addition salts and $C_1$-$C_6$ alkyl quaternary ammonium salts thereof.

Preferred compounds have the above formula wherein $R^1$ is hydroxy or $CONH_2$, n is 3, $R^2$ is hydrogen or $C_1$-$C_6$ alkyl and $R^3$ is $C_1$-$C_6$ alkyl.

According to this invention, a compound having the above formula, or a pharmaceutically acceptable salt thereof, is administered orally or parenterally to a subject suffering from an arrhythmia and in need of therapeutic treatment, or to a subject suspected of developing an arrhythmia and in need of prophylactic treatment.

Detailed Description of the Invention

In the above formula, $R^1$ is hydroxy, cyano or an aminocarbonyl group of the formula $CONR^4R^5$ in which $R^4$ and $R^5$ independently are hydrogen or $C_1$-$C_6$ alkyl. The method of this invention is preferably carried out utilizing compounds wherein $R^1$ is $CONH_2$. The method additionally utilizes compounds wherein one or both of $R^4$ and $R^5$ are $C_1$-$C_6$ alkyl such as methyl, ethyl, n-propyl, isopropyl, n-butyl, isobutyl, tert-butyl, n-pentyl, iso-pentyl, n-hexyl, 2-methylpentyl, and the like.

$R^2$ and $R^3$ are defined in the above formula to include hydrogen, $C_1$-$C_6$ alkyl such as those illustrated above for $R^4$ and $R^5$, and $CH_2C_2$-$C_5$ alkenyl such as allyl, 2-butenyl, 3-hexenyl, 2-methyl-3-pentenyl, 4-pentenyl, and related alkenyl groups. $R^2$ and $R^3$ additionally are phenyl-$C_1$-$C_3$ alkyl such as benzyl, 2-phenylethyl and 3-phenylpropyl. When $R^2$ and $R^3$ are taken together to form a $C_4$-$C_5$ alkylene chain, there is formed, in combination with the nitrogen atom to which $R^2$ and $R^3$ are attached, a cyclic moiety selected from pyrrolidino and piperidino. When $R^2$ and $R^3$ together are -$CH_2CH_2$-$O$-$CH_2CH_2$-, the contemplated cyclic system is morpholino.

The compounds defined by the above general formula are amines and as such are basic in nature, and consequently react with acids and alkylating agents to from salts. The pharmaceutically acceptable salts of the above-defined amines are useful as antiarrhythmic agents and are included within the scope of this invention. The term "pharmaceutically acceptable salt" refers to salts of the amine bases defined by the above formula which are substantially non-toxic to living organisms. Preferred pharmaceutically acceptable salts are those prepared by reacting an amine base of the above formula with an inorganic or organic acid. Commonly used inorganic acids include hydrochloric, hydrobromic, sulfuric, phosphoric, perchloric and related acids. Organic acids routinely utilized to form pharmaceutically acceptable acid addition salts include acetic, oxalic, butyric, succinic, malonic, citric, benzoic, fumaric, para-toluenesulfonic, and related organic acids.

Quaternary ammonium salts also are contemplated and are prepared by reacting a tertiary amine of the above formula, ie. wherein $R^2$ and $R^3$ both are other than hydrogen, with a lower alkyl alkylating agent. Commonly used alkylating agents are $C_1$-$C_6$ alkyl halides such as methyl chloride, n-butyl bromide, n-hexyl iodide and the like.

The 9-aminoalkylfluorenes defined by the above formula and utilized in the method of this invention can be prepared by any of a number of methods utilizing well known procedures. As already pointed out, certain of the fluorenes defined by the above formula wherein $R^1$ is hydroxy are known in the art. For example, British Pat. No. 960,758 discloses a number of 9-(3-dialkylaminopropyl)-9-hydroxyfluorenes. Such compounds can be prepared by reaction of fluoren-9-one with an aminoalkyl Grignard reagent such as dimethylaminopropyl magnesium bromide, diisopropylaminopropyl magnesium chloride, N-ethyl-N-isopropylaminopropyl magnesium iodide and the like. Such reactions are carried out in unreactive organic solvents such as diethyl ether or tetrahydrofuran to form, after normal decomposition of the Grignard complex and isolation of the product, the corresponding 9-aminoalkyl-9-hydroxyfluorene.

Such hydroxyfluorene compounds can alternatively be prepared by reacting fluoren-9-one with an alkali metal salt of an aminoalkyne to form the corresponding 9-aminoalkynyl-9-hydroxyfluorene, which upon hydrogenation gives the desired 9-aminoalkyl-9-hydroxyfluorene. For example, reaction of fluoren-9-one with 4-ethylaminobutynyl lithium provides 9-(4-ethylaminobutynyl)-9-hydroxyfluorene, which upon hydrogenation gives 9-(4-ethylaminobutyl)-9-hydroxyfluorene.

The 9-cyanofluorenes which are used in the method of this invention can be prepared by reacting 9-cyanofluorene with a strong base and an aminoalkyl alkylating agent such as an aminoalkyl halide. For example, 9-cyanofluorene reacts with a strong base such as n-butyl lithium or sodium amide to form the corresponding alkali metal salt of the 9-carbanion of 9-cyanofluorene. The carbanion then reacts with an alkylating agent such as 2-isopropylaminoethyl bromide or 3-piperidinopropyl chloride or 4-benzylaminobutyl iodide to afford the corresponding 9-aminoalkyl-9-cyanofluorene. Such alkylation reactions typically are carried out in unreactive organic solvents such as tetrahydrofuran, toluene or xylene, and are usually complete after about ten to twenty hours when carried out at about 50° to about 100° C. The product is isolated by simply diluting the reaction mixture with water, extracting the product into a suitable solvent such as diethyl ether, and then evaporating the solvent. Normal purification such as distillation or crystallization can be carried out if needed.

The 9-aminoalkyl-9-cyanofluorenes thus prepared are useful not only in the method of this invention, but additionally serve as intermediates in the preparation of the 9-aminoalkyl-9-aminocarbonylfluorenes, compounds having the above formula wherein $R^4$ and $R^5$ both hydrogen. For example, a 9-aminoalkyl-9-cyanofluorene can be hydrolyzed by reaction with an acid such as sulfuric acid at an elevated temperature of about 70° to about 100° C. for about one-half to three hours. The primary carboxamide that is formed can be isolated by making the reaction mixture alkaline, for instance by adding a base such as sodium hydroxide until the pH reaches about 10, and then extracting the product into a water immiscible solvent such as diethyl ether. Removal of the organic solvent by evaporation then provides the corresponding primary carboxamide, ie. a 9-aminoalkyl-9-aminocarbonylfluorene. Such compounds are of particular importance in the method of this invention.

The carboxamides of the above formula, including those wherein one or both of $R^4$ and $R^5$ are other than hydrogen, alternatively can be prepared by reacting a 9-aminoalkyl-9-halocarbonyl(or 9-alkoxycarbonyl)fluorene with an amine of the formula $HNR^4R^5$. For example, a fluorenyl carboxylic acid such as 9-(3-N-benzyl-N-isopropylaminopropyl-9-hydroxycarbonylfluorene can be reacted with oxalyl chloride to give the corresponding acid chloride, which readily reacts with an amine to give the corresponding carboxamide.

According to the method of treatment provided by this invention, the 9-aminoalkylfluorenes defined by the above formula are administered to a subject for the treatment of cardiac arrhythmia. The effectiveness of the compounds in such treatment has been determined by evaluating selected compounds of the above formula in biological assays designed to measure antiarrhythmic activity in animals. One such assay comprises administering a compound of unknown biological activity to a dog suffering from an experimentally induced cardiac arrhythmia, and observing whether or not the compound effects a conversion of the arrhythmia to a normal sinus rhythm, and if so, for how long the conversion persists.

In a typical experiment to determine the activity of the compounds used in the method of this invention, one or more mongrel dogs of either sex were anesthetized with sodium pentobarbital. A 23 gauge Butterfly infusion needle was placed in the radial vein for the introduction into the dog of sufficient ouabain to induce an arrhythmia, and for the introduction into the dog of the test compound. Each dog was continuously monitored throughout the experiment by electrocardiogram. After the ouabain induced cardiac arrhythmia had continued for thirty minutes, a 9-aminoalkylfluorene of the above formula was administered via the Butterfly infusion needle at the rate of 200 µg per kilogram of dog body weight per minute. If the arrhythmia was not converted to a normal sinus rhythm within ten minutes from the initial administration of test compound, as observed by electrocardiogram, the rate of infusion of test compound was increased to 500 µg per kilogram per minute. The amount of test compound required to convert an arrhythmia to normal rhythm was recorded as the "converting dose". Following the complete administration of test compound to the dog, the dog's heart was monitored by electrocardiogram until such time that an arrhythmia returned to the dog's heart, or for a maximum time of two hours, at which time the experiment was terminated. The duration of normal rhythm was recorded in minutes.

The results of several such experiments are set out in the following table. Most of the compounds were evaluated more than once, as indicated in the "No. of Dogs" column. The average converting dose is given in mg. per kilogram of animal body weight. Average duration of conversion is recorded in minutes.

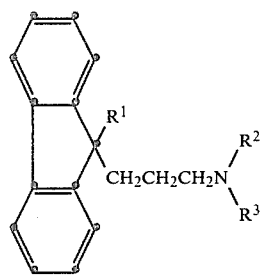

| R[1] | R[2] | R[3] | No. of dogs | Coverting dose mg/kg | Duration minutes |
| --- | --- | --- | --- | --- | --- |
| CONH$_2$ | H | i-Pr | 3 | 0.7 | 120 |
| OH | H | i-Pr | 4 | 2.1 | 104 |
| CONH$_2$ | CH$_3$ | CH$_3$ | 1 | 3.2 | 80 |
| OH | H | CH$_2$— | 2 | 1.9 | 18 |
| OH | CH$_3$ | CH$_3$ | 2 | 5.8 | 16 |
| OH | i-Pr | i-Pr | 3 | 2.2 | 68 |
| OH |  |  | 2 | 1.5 | 27 |

According to the method of this invention, the 9-aminoalkylfluorenes of the above formula are employed in combatting cardiac arrhythmias in animals by administering an antiarrhythmic amount of one or more of the aminoalkylfluorenes to an animal. The compounds are effective as antiarrhythmia agents when administered internally to an animal so as to introduce the compound into the animal's cardiovascular system. Parenteral administration of the compounds can be accomplished by intraperitoneal, subcutaneous or intravenous injection. The compounds alternatively can be administered orally in the form of tablets, capsules, elixirs, syrups, buccal seals and the like. The aminoalkylfluorenes have good antiarrhythmic activity both therapeutically, for instance when administered to an animal suffering from an arrhythmia and in need of treatment, and prophylactically when administered to an animal suspected of developing an arrhythmia, thereby protecting the animal against the occurrence or recurrence of arrhythmias.

The 9-aminoalkylfluorenes generally are utilized as pharmaceutical formulations. Such formulations ideally contain from about 1 to about 50 percent by weight of an aminoalkylfluorene in combination with a suitable pharmaceutical diluent, excipient or carrier therefor. Diluents commonly utilized in formulating the compounds in solid form suitable for oral administration include starch, lactose, gelatin, silica gel, rice flour, carboxymethyl cellulose and the like. Carriers employed in liquid formulations suitable for parenteral administration via the intravenous, intramuscular, or subcutaneous routes include water, saline, glucose syrup, ethanol, corn oil and the like.

The 9-aminoalkylfluorenes can be administered to a subject suffering from an arrhythmia and in need of treatment, or to a subject suspected of developing an arrhythmia and in need of prophylactic treatment. Parenteral administration may be preferred for subjects suffering from a life-threatening arrhythmia. Oral administration generally is preferred for maintenance or prophylactic treatment. The compounds ideally are formulated in such a way that the effective dose of 9-aminoalkylfluorene is an amount sufficient to treat the arrhythmia. Such doses typically will be from about 0.05 to about 25 mg/kg. A typical oral dose for the treatment of a patient suffering from an arrhythmia and weighing about 70 kg will be, for example, from about 3.5 to about 400 mg. of a suitably formulated aminoalkylfluorene, for instance 9-(3-isopropylaminopropyl)-9-aminocarbonylfluorene, preferably as a pharmaceutically acceptable acid addition salt such as the hydrochloride salt. Such oral dosing may be made from 1 to about 4 times each day, or as dictated by the particular patient and condition being treated. Such compound can of course be formulated for parenteral administration, for instance by intravenous infusion. Such formulation can be prepared by dissolving about 500 mg. of the above-noted or related compound in a suitable diluent such as 1000 ml. of 5 percent glucose. Such solution can be infused into a patient suffering from an arrhythmia at the rate of about 1 ml. per minute.

The preparation of the aminoalkylfluorenes used in the method of this invention is more fully described in the following detailed examples. It is to be understood, however, that the examples are illustrative of the compounds to be utilized in the method and are not to be construed as limiting the invention to the particular compounds or methods specifically described.

EXAMPLE 1

9-(3-Isopropylaminopropyl)-9-hydroxyfluorene

A solution of 9.0 g. of fluoren-9-one dissolved in 500 ml. of tetrahydrofuran was added dropwise over one hour to a stirred cold (−80° C.) solution of 500 ml. of tetrahydrofuran containing 9.7 g. of 3-isopropylaminopropyne and 75 ml. of a 1.6 molar tetrahydrofuran solution of n-butyl lithium. After the addition was complete, the reaction mixture was warmed to room temperature and then heated to reflux for sixteen hours. The reaction mixture was next cooled to room temperature and diluted by the dropwise addition of 200 ml. of water. The aqueous mixture was extracted several times with diethyl ether, and the ethereal extracts were combined, and the reaction product was converted to the hydrochloride salt by the addition of 300 ml. of 6 N hydrochloric acid to the ethereal solution. The aqueous acid layer containing the reaction product was separated, washed once with fresh diethyl ether, and then made alkaline by the addition of 10 percent sodium hydroxide, which effected liberation of the hydrochloride salt back to the free amine. The free amine was extracted into fresh diethyl ether. The ethereal extracts were combined, washed with water and dried. Removal of the solvent by evaporation under reduced pressure then afforded 2.3 g. of 9-(3-isopropylaminopropynyl)-9-hydroxyfluorene. M.P. 214°–215° C.

A solution of 2.3 g. of 9-(3-isopropylaminopropynyl)-9-hydroxyfluorene in 200 ml. of ethanol containing 3.0 g. of five percent palladium on carbon was agitated at room temperature for six hours under a hydrogen atmosphere of 60 psi. The reaction mixture then was filtered to remove the catalyst, and the filtrate was concentrated to dryness by evaporation of the solvent under reduced pressure. The solid that was thus obtained was crystallized from ethyl acetate and skelly B to afford 1.6 g. of 9-(3-isopropylaminopropyl)-9-hydroxyfluorene. M.P. 135°–137° C.

Analysis calc. for $C_{19}H_{23}NO$. Theory: C, 81.10; H, 8.24; N, 4.98. Found: C, 81.17; H, 8.38; N, 4.72.

EXAMPLE 2–6

Following the procedure set forth in Example 1, fluorene-9-one was reacted with the appropriate aminoalkyne and strong base to give the corresponding 9-aminoalkynyl-9-hydroxyfluorene, which upon hydrogenation afforded the following compounds:

9-[3-(N-benzyl-N-isopropylamino)propyl]-9-hydroxyfluorene. M.P. 68°–70°.

Analysis calc. for $C_{26}H_{29}NO$. Theory: C, 84.06; H, 7.87; N, 3.77. Found: C, 84.15; H, 7.70; N, 3.54.

9-[3-(N-isopropyl-N-methylamino)propyl]-9-hydroxyfluorene. M.P. 71°–72° C.

Analysis calc. for $C_{20}H_{25}NO$. Theory: C, 81.31; H, 8.53; N, 4.74. Found: C, 81.16; H, 8.29; N, 4.48.

9-(3-pyrrolidinopropyl)-9-hydroxyfluorene. M.P. 118°–120° C.

Analysis calc. for $C_{20}H_{23}NO$. Theory: C, 81.87; H, 7.90; N, 4.77. Found: C, 82.10; H, 7.82; N, 4.96.

9-(3-N,N-dimethylaminopropyl)-9-hydroxyfluorene. M.P. 99°–101° C.

Analysis calc. for $C_{18}H_{21}NO$. Theory: C, 80.86; H, 7.92; N, 5.24. Found: C, 80.89; H, 7.90; N, 5.07.

9-(3-N,N-diisopropylaminopropyl)-9-hydroxyfluorene hydrochloride. M.P. 202°–205° C.

Analysis calc. for $C_{22}H_{30}NOCl$. Theory: C, 73.41; H, 8.40; N, 3.89. Found: C, 73.49; H, 8.19; N, 3.76.

EXAMPLE 7

9-(3-Dimethylaminopropyl)-9-cyanofluorene

To a stirred solution of 2.6 g. of sodium amide in 200 ml. of tetrahydrofuran was added dropwise over thirty minutes a solution of 12.7 g. of 9-cyanofluorene in 300 ml. of tetrahydrofuran. The reaction mixture was next heated to reflux for three hours, and then cooled to room temperature. While the reaction mixture was being stirred at room temperature, a solution of 14.2 g. of 3-dimethylaminopropyl chloride in 500 ml. of tetrahydrofuran was added dropwise over one hour. Following complete addition, the reaction mixture was again heated to reflux and stirred for sixteen hours. After cooling the mixture to room temperature, it was added to 500 ml. of water. The product was extracted into diethyl ether, and the ethereal extracts were combined, washed with water and dried. Removal of the solvent by evaporation under reduced pressure afforded, after distillation, 2.3 g. of 9-(3-dimethylaminopropyl)-9-cyanofluorene. B.P. 195°–201° C. at 0.1 torr.

EXAMPLES 8–12

The following 9-aminoalkyl-9-cyanofluorenes were prepared by reacting 9-cyanofluorene with the appropriate aminoalkyl halide according to the procedure of Example 7.

9-(2-N-Benzyl-N-isopropylaminoethyl)-9-cyanofluorene. B.P. 200°–210° C. at 0.11 torr.

Analysis calc. for $C_{26}H_{26}N_2$. Theory: C, 85.21; H, 7.15; N, 7.64. Found: C, 84.94; H, 6.85; N, 7.44.

9-(3-Piperidinopropyl)-9-cyanofluorene. B.P. 200°–208° C. at 0.18 torr.

9-(3-Diethylaminopropyl)-9-cyanofluorene. B.P. 182°–195° C. at 0.18 torr.

9-(3-N-Benzyl-N-isopropylaminopropyl)-9-cyanofluorene. B.P. 220°–245° C. at 0.18 torr.

9-(3-Isopropylaminopropyl)-9-cyanofluorene.

EXAMPLE 13

9-(3-Isopropylaminopropyl)-9-aminocarbonylfluorene

A solution of 2.5 g. of 9-(3-isopropylaminopropyl)-9-cyanofluorene in 20 ml. of concentrated sulfuric acid and 8 ml. of water was heated at 100° C. for forty-five minutes. The reaction mixture then was added to 50 g. of ice, and 10 percent aqueous sodium hydroxide was added to pH=10. The alkaline mixture was extracted several times with diethyl ether. The ethereal extracts were combined, washed with water and dried. Removal of the solvent by evaporation under reduced pressure provided a white solid, which after crystallization from skelly B afforded 1.2 g. of 9-(3-isopropylaminopropyl)-9-aminocarbonylfluorene. M.P. 94°–95° C.

Analysis calc. for $C_{20}H_{24}N_2O$. Theory: C, 77.89; H, 7.84; N, 9.08. Found: C, 78.17; H, 7.65; N, 9.00.

EXAMPLES 14–17

The following fluorene carboxamides were prepared by acid hydrolysis of the corresponding fluorene nitrile according to the procedure of Example 13.

9-(3-Piperidinopropyl)-9-aminocarbonylfluorene. M.P. 155°–156.5° C.

Analysis clac. for $C_{22}H_{26}N_2O$. Theory: C, 79.00; H, 7.84; N, 8.38. Found: C, 78.73; H, 7.70; N, 8.14.

9-(3-Dimethylaminopropyl)-9-aminocarbonylfluorene. M.P. 91°–92° C.

Analysis calc. for $C_{19}H_{22}N_2O$. Theory: C, 77.52; H, 7.53; N, 9.52. Found: C, 77.51; H, 7.50; N, 9.29.

9-(3-Diethylaminopropyl)-9-aminocarbonylfluorene. M.P. 78°–79° C.

Analysis calc. for $C_{20}H_{26}N_2O$. Theory: C, 78.22; H, 8.13; N, 8.69. Found: C, 78.43; H, 8.11; N, 8.59.

9-(3-N-Benzyl-N-isopropylaminopropyl)-9-aminocarbonylfluorene.

EXAMPLE 18

9-(2-Isopropylaminoethyl)-9-cyanofluorene

A solution of 3.0 g. of five percent palladium on charcoal in 200 ml. of ethanol containing 7.3 g. of 9-(2-N-benzyl-N-isopropylaminoethyl)-9-cyanofluorene (the compound prepared in Example 8) was agitated for twelve hours at 40° C. under a hydrogen atmosphere of 60 psi. The reaction mixture was filtered and the solvent was evaporated from the filtrate to provide a gum. The gum was crystallized from skelly B to afford 3.2 g. of 9-(2-isopropylaminoethyl)-9-cyanofluorene. M.P. 150°–152° C.

EXAMPLE 19

Following the procedure of Example 18, 27.5 g. of 9-(3-N-benzyl-N-isopropylaminopropyl)-9-cyanofluorene was hydrogenated in the presence of 3.0 g. of five percent palladium on charcoal to give 23.4 g. of 9-(3-isopropylaminopropyl)-9-cyanofluorene. M+ 290; theory 290.

EXAMPLE 20

9-(3-Isopropylaminopropyl)-9-aminocarbonylfluorene hydrochloride

Hydrogen chloride was bubbled through a solution of 2.357 g. of 9-(3-isopropylaminopropyl)-9-aminocarbonylfluorene in 150 ml. of ethanol. The solution was stirred at ambient temperature for five minutes, and then concentrated by evaporation of the solvent under reduced pressure. The solid thus formed was recrystallized from ethanol and diethyl ether to give 2.145 g. of 9-(3-isopropylaminopropyl)-9-aminocarbonylfluorene hydrochloride. M.P. 203°–204° C.

Analysis calc. for $C_{20}H_{25}N_2OCl$. Theory: C, 69.65; H, 7.31; N, 8.12. Found: C, 69.94; H, 7.58; N, 8.39.

EXAMPLE 21

9-(3-N-Isopropyl-N-methylaminopropyl)-9-hydroxyfluorene methiodide.

A solution of 2.7 g. of 9-(3-N-isopropyl-N-methylaminopropyl)-9-hydroxyfluorene in 20 ml. of ethanol containing 1.1 g. of methyl iodide was stirred at ambient temperature for thirty minutes. The precipitated solid was collected by filtration and recrystallized from fresh ethanol to afford 2.5 g. of 9-(3-N-isopropyl-N-methylaminopropyl)-9-hydroxyfluorene methiodide. M.P. 217°–219° C.

Analysis calc for $C_{21}H_{28}NOI$. Theory: C, 57.67; H, 6.45; N, 3.20. Found: C, 57.65; H, 6.30; N, 3.22.

EXAMPLE 22

Following the procedure of Example 21, 9-(3-N-isopropyl-N-methylaminopropyl)-9-aminocarbonylfluorene was reacted with allyl bromide in dichloromethane to give the corresponding quaternary ammonium salt, namely 9-(3-N-allyl-N-isopropylaminopropyl)-9-aminocarbonylfluorene methyl bromide.

EXAMPLE 23

9-(4-N-Benzyl-N-isopropylaminobutyl)-9-ethylaminocarbonylfluorene

To a stirred solution of 9-(4-N-benzyl-N-isopropylaminobutyl)-9-hydroxycarbonylfluorene in benzene is added oxalyl chloride. The reaction is stirred for several hours and then the solvent is evaporated to give 9-(4-N-benzyl-N-isopropylaminobutyl)-9-chlorocarbonylfluorene as an oil. The oil thus formed is dissolved in dichloromethane containing triethylamine and stirred while ethylamine is added in one portion. After stirring the reaction mixture several hours, the solvent is removed to provide the corresponding N-alkyl amide, namely, 9-(4-N-benzyl-N-isopropylaminobutyl)-9-ethylaminocarbonylfluorene. Debenzylation by hydrogenation in the presence of palladium on carbon affords 9-(4-isopropylaminobutyl)-9-ethylaminocarbonylfluorene.

EXAMPLE 24

The following formulation is suitable for oral therapeutic and maintenance therapy of a human suffering from an arrhythmia and in need of treatment.

| Ingredient | amount |
|---|---|
| 9-(3-isopropylaminopropyl)-9-aminocarbonylfluorene hydrochloride | 50 mg |
| Lactose | 100 mg |
| Corn starch | 10 mg |

The ingredients are blended together with suitable granulating agents and binders and molded into tablet form. Such tablets can be administered from 1 to 4 times a day for the treatment of arrhythmia.

EXAMPLE 25

The following preparation is suitable for parenteral administration to a subject in need of antiarrhythmic treatment.

| Ingredient | amount |
|---|---|
| 9-(4-N,N-diethylaminobutyl)-9-hydroxyfluorene | 20.0 grams |
| propylene glycol | 700.0 ml. |
| sterile water | 200.0 ml. |

The ingredients are mixed and the pH of the solution is adjusted to about 5 with hydrochloric acid, and then the volume is adjusted to 1000 ml by the addition of sterile water. The formulation is sterilized, filled into 5.0 ml. ampoules each containing 2.0 ml., (40 mg. of active drug) and sealed under nitrogen.

We claim:

1. A method for treating cardiac arrhythmias comprising administering to a subject suffering from an arrhythmia and in need of treatment or to a subject suspected of being prone toward developing a cardiac arrhythmia and in need of prophylactic treatment an antiarrhythmic amount of a compound of the formula

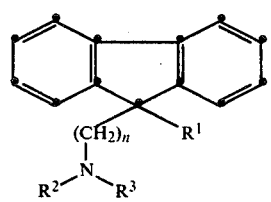

wherein:
$R^1$ is hydroxy, cyano or $CONR^4R^5$ in which $R^4$ and $R^5$ independently are hydrogen or $C_1$-$C_6$ alkyl; n is 2, 3 or 4;
$R^2$ and $R^3$ independently are hydrogen, $C_1$-$C_6$ alkyl, $CH_2C_2$-$C_5$ alkenyl, phenyl-$C_1$-$C_3$ alkyl, or taken together are $C_4$-$C_5$ alkylene or —$CH_2CH_2$—O—$CH_2CH_2$—; or the pharmaceutically acceptable acid addition salts or $C_1$-$C_6$ quaternary ammonium salts thereof.

2. The method of claim 1 wherein in the compound administered, $R^1$ is hydroxy.

3. The method of claim 2 wherein in the compound administered, n is 3.

4. The method of claim 3 wherein in the compound administered, $R^2$ is hydrogen and $R^3$ is $C_1$-$C_6$ alkyl.

5. The method of claim 4 wherein in the compound administered, $R^3$ is methyl, ethyl or isopropyl.

6. The method of claim 3 wherein in the compound administered, $R^2$ and $R^3$ both are other than hydrogen.

7. The method of claim 6 wherein in the compound administered, $R^2$ and $R^3$ both are methyl or ethyl.

8. The method of claim 1 wherein in the compound administered, $R^1$ is cyano.

9. The method of claim 8 wherein in the compound administered, $R^2$ is hydrogen and $R^3$ is $C_1$-$C_6$ alkyl.

10. The method of claim 9 wherein in the compound administered, $R^3$ is methyl, ethyl or isopropyl.

11. The method of claim 8 wherein in the compound administered, $R^2$ and $R^3$ both are other than hydrogen.

12. The method of claim 1 wherein in the compound administered, $R^1$ is $CONR^4R^5$.

13. The method of claim 12 wherein in the compound administered, $R^4$ is hydrogen.

14. The method of claim 13 wherein in the compound administered, $R^5$ is hydrogen.

15. The method of claim 14 wherein in the compound administered, $R^2$ is hydrogen.

16. The method of claim 15 wherein in the compound administered, n is 3.

17. The method of claim 16 wherein in the compound administered, $R^3$ is $C_1$-$C_6$ alkyl.

18. The method of claim 17 wherein in the compound administered, $R^3$ is methyl or ethyl.

19. The method of claim 17 wherein in the compound administered, $R^3$ is iso-propyl.

20. The method of claim 1 wherein the compound administered is a pharmaceutically acceptable acid addition salt.

21. The method of claim 1 wherein the compound administered is a pharmaceutically acceptable quaternary ammonium salt.

* * * * *